(12) United States Patent
Han et al.

(10) Patent No.: US 6,709,568 B2
(45) Date of Patent: Mar. 23, 2004

(54) METHOD FOR DETERMINING CONCENTRATIONS OF ADDITIVES IN ACID COPPER ELECTROCHEMICAL DEPOSITION BATHS

(75) Inventors: Jianwen Han, Danbury, CT (US); Ronni M. Etterman, Portland, OR (US); Peter M. Robertson, Winkel (CH); Richard Bhella, Gilbert, AZ (US); David Price, Austin, TX (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/064,125

(22) Filed: Jun. 13, 2002

(65) Prior Publication Data

US 2003/0230485 A1 Dec. 18, 2003

(51) Int. Cl.⁷ ............................................. G01N 27/42
(52) U.S. Cl. .......................... 205/775; 205/81; 205/83; 205/780.5; 205/786.5; 204/434
(58) Field of Search ............................. 205/81, 83, 775, 205/780.5, 786.5, 791, 794; 204/434

(56) References Cited

U.S. PATENT DOCUMENTS

| | | | |
|---|---|---|---|
| 2,707,166 A | | 4/1955 | Brown et al. |
| 2,707,167 A | | 4/1955 | Hoover |
| 2,830,014 A | | 4/1958 | Gundel et al. |
| 3,101,305 A | | 8/1963 | Roth et al. |
| 3,276,979 A | | 10/1966 | Strauss et al. |
| 3,288,690 A | | 11/1966 | Creutz et al. |
| 3,655,534 A | * | 4/1972 | Kampe ........................ 205/307 |
| 3,725,220 A | | 4/1973 | Kessler et al. |
| 3,798,138 A | | 3/1974 | Ostrow et al. |
| 3,972,789 A | * | 8/1976 | Eppensteiner et al. ...... 205/307 |
| 4,038,161 A | * | 7/1977 | Eckles et al. ................ 205/298 |
| 4,132,605 A | * | 1/1979 | Tench et al. ................. 205/787 |
| 4,917,774 A | * | 4/1990 | Fisher ......................... 205/787 |
| 4,917,777 A | * | 4/1990 | Fisher ......................... 205/787 |
| 5,223,118 A | * | 6/1993 | Sonnenberg et al. .......... 205/81 |
| 5,320,724 A | * | 6/1994 | Ludwig et al. .......... 205/780.5 |
| 6,280,602 B1 | * | 8/2001 | Robertson .................... 205/775 |
| 6,592,737 B1 | * | 7/2003 | Robertson ..................... 205/81 |

OTHER PUBLICATIONS

Kruglikov, S.S. et al, Electrochimica Acta, 1967, vol. 12, pp. 1263–1271.*

* cited by examiner

Primary Examiner—Kaj K. Olsen
(74) Attorney, Agent, or Firm—Margaret Chappuis; Steven J. Hultquist

(57) ABSTRACT

The present invention relates to a method for determining concentration of brightener and leveler contained in an aqueous acid metal electroplating solution, by firstly determining the concentration of the brightener at a first set of measurement conditions, and secondly determining the concentration of the leveler at a second set of measurement conditions, provided that the first set of measurement conditions differ from the second set of measurement conditions on the rotation speed of a rotating disc electrode used for measuring plating potential of said aqueous acid metal electroplating solution, and optionally, the electroplating duration at which the plating potential of said aqueous acid metal electroplating solution is measured, provided that the first rotation speed is lower than the second rotation speed, and that the first electroplating duration is shorter than the second electroplating duration.

20 Claims, 11 Drawing Sheets

METHOD FOR DETERMINING CONCENTRATIONS OF ADDITIVES IN ACID COPPER ELECTROCHEMICAL DEPOSITION BATHS

BACKGROUND OF INVENTION

1. Field of Invention

The present invention in a broad aspect relates to quantitative analysis of concentration of additives contained in a metal electroplating solution, and more specifically to a method for determining concentration of brightener and leveler in aqueous acid copper electroplating solutions.

2. Related Art

Traditionally, aluminum (Al) has been used as the material of choice for metalization in forming interconnect layers in the manufacture of semiconductor microelectronic integrated circuits. Al is commonly deposited on semiconductor structures by chemical vapor deposition (CVD), which allows for precise control and highly uniform deposition of the product metal-containing film.

Despite the prior ubiquity of Al as a metalization medium, performance demands associated with increasing signal speeds and decreasing feature geometries of microelectronics have exceeded the capabilities of Al metal. Copper (Cu) therefore is increasingly being utilized as a semiconductor interconnect metal. The properties of Cu are not amenable to conventional CVD metalization approaches, due in part to the lack of suitable copper source reagents, and in consequence Cu is typically deposited on the microelectronic device structure via electroplating.

Electroplating of copper, however, has various associated problems.

Generally, Cu is plated onto a substrate by electrolysis in an aqueous acid copper plating solution, which may for example comprise copper sulfate, sulfuric acid, and hydrochloric acid. The plating process with an unaugmented plating solution of such type normally proceeds too rapidly. The result of such plating rapidity is that previously formed vias, i.e., passages to lower-level structures, e.g., electrodes or other conductors or semiconductor regions in the microelectronic device structure, are bridged over, and not filled with Cu. Accordingly, the desired electrical path to the underlying structure is not formed, and the semiconductor device structure must be reworked or discarded.

In order to produce a brilliant copper finish on the plating surface of the microelectronic devices, various brighteners have to be added to the acidic electroplating solutions. Such brighteners usually comprise organic sulfonic and carboxylic acids, or their salts, and the use of such brighteners results in improved stability of the copper electroplating solutions and effective deposition of copper over a satisfactory current density range. For more details about suitable brighteners, see U.S. Pat. Nos. 2,707,166, 2,707,167, 2,830,014, 3,276,979, and 3,288,690.

The addition of brightener or brighteners alone, although resulting in a sufficiently brilliant finish, does not guarantee a smooth copper deposit layer on the plating surface of the microelectronic devices, if such plating surface contains small recesses or protrusions caused by microscopic cracks or scratches. In order to eliminate the effect of such microscopic cracks or scratches, levelers need to be further added to the copper electroplating solutions, which will give such electroplating solutions the "leveling" ability to produce relatively thicker layer of copper deposits in small recesses and relative thinner layer of copper deposits on small protrusions, thereby decreasing the depth of plating surface irregularities. Levelers known in the art include thiourea derivatives, condensation of thiourea with aliphatic aldehydes such as formaldehyde, and heterocyclic sulfurnitrogen organic compounds, as disclosed in U.S. Pat. Nos. 3,101,305, 3,655,534, 3,725,220, 3,798,138, 3,972,789, and 4,038,161.

The speed of copper deposition and the quality and electrical and mechanical properties of the resulting copper deposits are critically dependent on the concentration of the additives such as brighteners and levelers. However, the concentration of these additives is not constant, due to either "drag-out" by the microelectronic devices, or by electrochemical reaction and loss during the plating process. Therefore, precise real-time chemical concentration monitoring and control of the electroplating solutions are vital for producing high quality copper films or structures on microelectronic devices.

Precise monitoring of the concentration of the organic brighteners and levelers in a copper plating solution faces various difficulties. For example, the respective concentrations of the brighteners and levelers in the copper electroplating solutions are usually very low, e.g., part-per-million by volume (ppmv), which makes normal analytical procedures difficult to effectively apply, due to the masking effect of the high concentration of inorganic components such as copper sulfate and acids.

U.S. Pat. No. 6,280,602 discloses a method and apparatus for calculating the concentration of organic additives in a sample of metal plating solution, by measuring the plating potential of such solution and performing Pulsed Cyclic Galvanostatic Analysis on the measured plating potential. The content of such patent is incorporated by reference herein in its entirety for all purposes.

One problem that the U.S. Pat. No. 6,280,602 did not address is the interaction between the brightening effects of the brightener and the leveling effects of the leveler. The brightener usually accelerates the electroplating process, and the leveler, on the other hand, slows down the electroplating process. The cross-interference of the brightening effects and the leveling effects leads to inaccuracy of the concentration as calculated according to the method disclosed by U.S. Pat. No. 6,280,602.

It would therefore be a significant advance in the art, and is accordingly an object of the present invention, to provide a method for determining the concentration of the brightener and the leveler in an acid metal electroplating solutions, while reducing or minimizing the cross-interference between the effects of the brightener and the leveler, relative to the present state of the art.

Other objects and advantages will be more fully apparent from the ensuring disclosure and appended claims.

SUMMARY OF INVENTION

The present invention in a broad aspect relates to a method for determining concentration of brightener and leveler contained in an aqueous acid metal electroplating solution, comprising the steps of:

(a) providing a measuring apparatus that comprises:
   (i) a reference electrode;
   (ii) a rotating disc test electrode having a plating surface for depositing metal thereon and a rotational driver for rotating such rotating disc test electrode at a predetermined rotation speed, wherein such rotating disc electrode is disposed in a measurement chamber that comprises an electroplating current source electrode, and wherein the aqueous acid metal electroplating solution is introduced into the measurement chamber for measurement;

(iii) electroplating-driving electronics that are electrically and operatively coupled between the rotating disc test electrode and the electroplating current source electrode, whereby metal is selectively deposited onto the plating surface of the rotating disc test electrode from the aqueous acid metal electroplating solution in the measurement chamber at a constant known current density; and (iv) measuring circuitry electrically and operatively coupled between the rotating disc test electrode and the reference electrode for measuring the electrical potential between the rotating disc test electrode and the reference electrode;

(b) determining the concentration of brightener in the aqueous acid metal electroplating solution, by using the measuring apparatus mentioned hereinabove to measure a first electrical potential of the metal electroplating solution at a first rotation speed and for a first electroplating duration, and by performing Pulsed Cyclic Galvanostatic Analysis of the first electrical potential as disclosed by U.S. Pat. No. 6,280,602; and (c) determining the concentration of leveler in the aqueous acid metal electroplating solution, by using said measuring apparatus to measure a second electrical potential of said metal electroplating solution at a second rotation speed for a second electroplating duration, and by performing Pulsed Cyclic Galvanostatic Analysis of the second electrical potential, wherein the first rotation speed is lower than the second rotation speed, and wherein the first electroplating duration is shorter than the second electroplating duration.

The present inventors have discovered that the brightening effect of the brightener is generally unaffected by and independent of the rotation speed of the rotating disc test electrode and the electroplating duration, while the leveling effect of the leveler is significantly increased at higher rotation speed and longer electroplating duration. Therefore, the cross-interference between the brightening effect and the leveling effect can be reduced or minimized, by firstly determining the concentration of the brightener at a lower rotation speed and/or for shorter electroplating duration, whereby the leveling effect of the leveler is less significant and therefore interferes less with the effect of the brightener, and then determining the concentration of the leveler at a higher rotation speed and/or for longer electroplating duration, wherein the leveling effect of the leveler is better manifested, while the brightening effect of the brightener remains approximately the same.

Preferably, the concentration of the brightener is first determined when the rotation speed of the rotating disc test electrode is set within a range of from about 0 rpm to about 4000 rpm, more preferably from about 0 rpm to about 2400 rpm, and/or the electroplating duration of the plating cycle is set within a range of from about 1 second to about 20 seconds, more preferably from about 1 second to about 10 seconds. The concentration of the leveler is then determined when the rotation speed of the rotating disc test electrode is preferably set within a range of from about 300 rpm to about 1250 rpm, more preferably from about 500 rpm to about 1250 rpm, and/or the electroplating duration is preferably set within a range of from about 1 second to about 25 seconds, more preferably from about 1 second to about 15 seconds.

Another aspect of the present invention involves a method for determining concentration of brightener and leveler contained in an aqueous acid metal electroplating solution, comprising the steps of:

(a) determining concentration of the brightener under a first set of measurement conditions;

(b) determining concentration of the leveler under a second set of measurement conditions, wherein the first set and second set of measurement conditions differ in at least one of the following measurement variables:

(i) rotation speed of a rotating disc electrode used for measuring plating potential of such aqueous acid metal electroplating solution; and (ii) electroplating duration at which the plating potential of such aqueous acid metal electroplating solution is measured.

Preferably, the first set of measurement conditions includes a rotation speed of the rotating disc test electrode that is lower than that of the second set of measurement conditions, and/or an electroplating duration that is shorter than that of the second set of measurement conditions.

A further aspect of the present invention relates to a method for determining concentration of a first additive and a second additive contained in a metal electroplating solution, comprising the steps of:

(a) determining concentration of the first additive in the metal electroplating solution under a first set of measurement conditions;

(b) determining concentration of the second additive in the metal electroplating solution under a second set of measurement conditions, wherein the first and second sets of measurement conditions differ from one another in at least one of the following measurement variables:

(i) rotation speed of a rotating disc electrode used for measuring plating potential of such metal electroplating solution; and (ii) electroplating duration at which the plating potential of such metal electroplating solution is measured.

The first and second additives can be any additives that have interfering effects on the plating capability of the metal electroplating solution, including but not limited to brighteners and levelers.

Additional aspects, features and embodiments of the invention will be more fully apparent from the ensuing disclosure and appended claims.

DETAILED DESCRIPTION

The measuring apparatus used for measuring the plating potentials for the Pulsed Cyclic Galvanostatic Analysis in the present invention may have any suitable structure or components, and the disclosure herein is not intended to be narrowly construed or interpreted regarding the broad scope of the present invention.

Preferably, such measuring apparatus comprises:

a reference electrode;

a rotating disc test electrode having a plating surface for depositing metal thereon and a rotational driver for rotating said rotating disc test electrode at a predetermined rotation speed, wherein said rotating disc electrode is disposed in a measurement chamber that comprises an electroplating current source electrode, and wherein the aqueous acid metal electroplating solution is introduced into the measurement chamber for measurement;

electroplating-driving electronics that are electrically and operatively coupled between the rotating disc test electrode and the electroplating current source electrode, whereby metal is selectively deposited onto the plating surface of said rotating disc test electrode from the aqueous acid metal electroplating solution in the measurement chamber at a constant known current density; and measuring circuitry electrically and operatively coupled between the rotating disc test electrode and the reference electrode for measuring the electrical potential between the rotating disc test electrode and the reference electrode.

Preferred embodiments of the measuring apparatus useful for practicing the present invention are disclosed by U.S. Pat. No. 6,280,602, and pending U.S. patent application Ser. No. 09/690,770, filed on Oct. 17, 2000 in the name of Peter M. Robertson, the entire contents of which hereby are incorporated herein by reference for all purposes.

Figure 1:
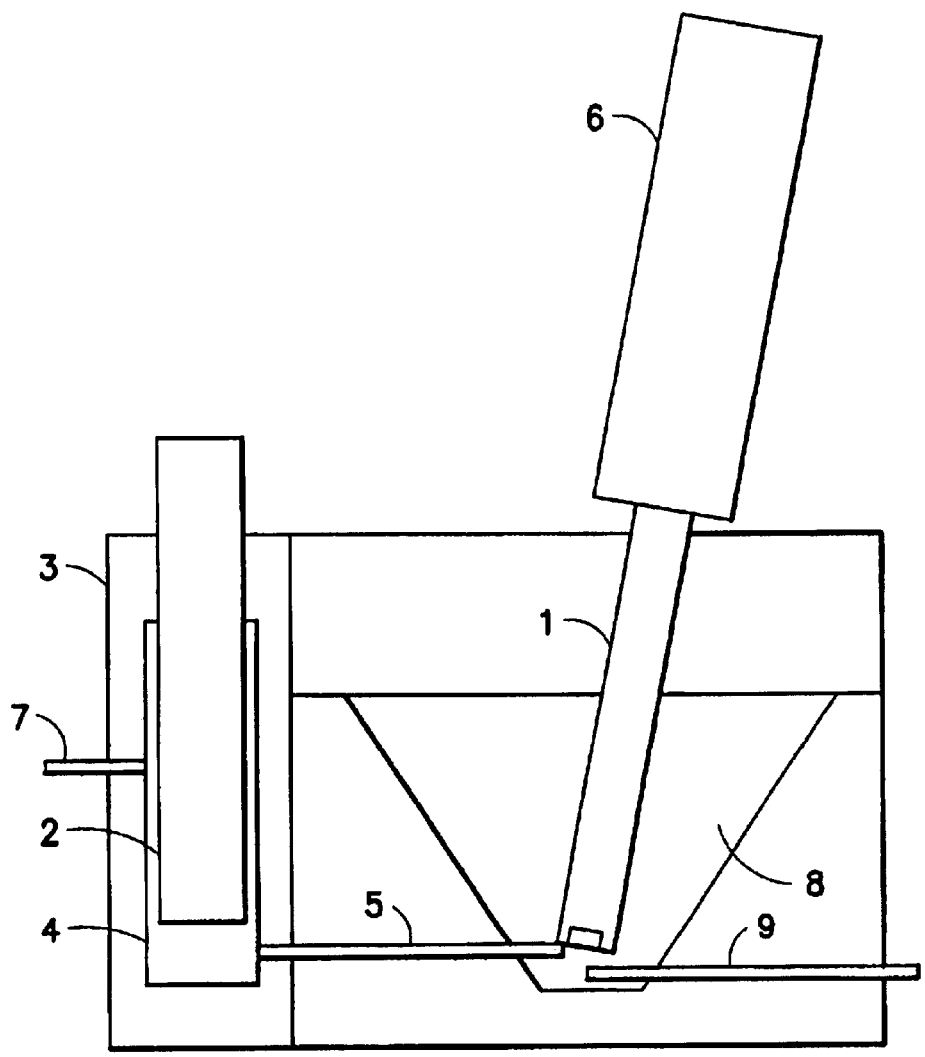
FIG. 1 is a schematic representation of a measuring apparatus used in the present invention according to one embodiment thereof.

Specifically, such measuring apparatus as shown in FIG. 1 comprises a reference electrode 2 disposed in a reference chamber 3, and continuously immersed in a base copper plating electrolyte solution 4. Base solution 4 is injected into reference chamber 3 through fluid flow inlet 7, and flows into measuring chamber 8 via capillary tube 5. Additional solutions containing brightener(s) and leveler(s) (i.e., sample solution and calibration solution(s)) are introduced into the measuring chamber (through means not depicted in FIG. 1) and thereby mixed with the base copper plating electrolyte solution introduced therein through capillary tube 5. Fluid pressure differential, and/or fluid flow valves prevent the propagation of mixed electrolyte solution from measuring chamber 8 to reference chamber 3. Thus, reference electrode 2 is continuously, exclusively immersed in base copper plating electrolyte solution 4.

The measuring chamber end of capillary tube 5 is disposed in close proximity to the plating surface of a test electrode 1, preferably within 20 mm, more preferably within 10 mm, and most preferably within 5 mm. This close spatial relationship prevents air bubble formation on the plating surface of test electrode 1, and reduces or eliminates the effect of potential difference (iR drop) in the electrolyte. Plating current source electrode 9 is electrically and operatively coupled to test electrode 1 through a suitable, reversible, controllable current source (not shown). Test electrode 1 is preferably comprised of a platinum or glassy carbon (vitreous carbon) substrate, although it is not restricted to these materials. Test electrode 1 is preferably a rotating disc electrode that has a rotational driver 6. Use of the rotating disk electrode increases the accuracy and consistency of measurements across cycles by stirring the electrolyte solution contained in the measurement chamber. The rotating disc test electrode 1 is preferably tilted at an angle from vertical, to prevent the collection and retention of air bubbles on its surface. Suitable means (not shown in FIG. 1) for measuring electrical potential between the test electrode and the reference electrode are employed.

Suitable means for introducing electroplating solutions that contain additives such as brightener and leveler into the measurement chamber 8, as well as suitable means for purging measurement chamber 8, while not shown in FIG. 1, are employed. Additionally, acid bath and rinsing water may be injected into and drained from the measurement chamber following completion of each plating cycle, and a forced fluid purging means (not shown) may optionally be provided. These ancillary functions are easily provided by means well known in the art, and are not shown in FIG. 1 or discussed at length in the present disclosure.

The Pulsed Cyclic Galvanostatic Analysis (PCGA) method as introduced in U.S. Pat. No. 6,280,602 is suitably utilized for calculating the concentration of additives in the target acid copper electroplating solution, by performing multiple plating/measurement cycles in mixed electroplating solutions containing various known and unknown concentrations of additives, using the measuring apparatus described hereinabove. In each plating/measurement cycle, the rotating disc test electrode and the measuring chamber are first thoroughly cleaned, e.g., electrolytically in an acid bath followed by a water and/or forced air flush. Base electrolyte solution is then introduced into the measuring chamber from the reference chamber, mixed with an electroplating solution that contains the additives, and the rotating disc test electrode is allowed to equilibrate. Cu is then deposited onto a plating surface on the rotating disc test electrode by electroplating in the mixed electrolyte solution for a predetermined plating duration, at a predetermined rotating speed and a known or constant current density. The decisive electrical potential between the rotating disc test electrode and reference electrode is then measured after expiration of the predetermined plating duration. The deposited Cu is then stripped from the test electrode by reverse biasing the electroplating circuit and/or by chemical stripping. Concentration of a target additive in the target copper electroplating solution is calculated indirectly, by performing multipleplating/measurement cycles using calibration electroplating solutions to construct a calibration curve between concentration of the target additive and the decisive electrical potentials measured, and then measuring the decisive electrical potential of the target electroplating solution to extrapolate the concentration of the target additive in the target electroplating solution based on the calibration curve that is constructed. For more details about PCGA, please see U.S. Pat. No. 6,280,602.

As stated hereinabove, the respective effects of the brightener and the leveler interference with each other, resulting in inaccurate determination of the concentration. The present invention provides a method for reducing or minimizing such interference, based on the discovery that the brightening effect of the brightener is generally unaffected by and independent of the rotation speed of the rotating disc test electrode and the electroplating duration, while the leveling effect of the leveler is significantly increased at higher rotation speed and longer electroplating duration.

Figure 2:
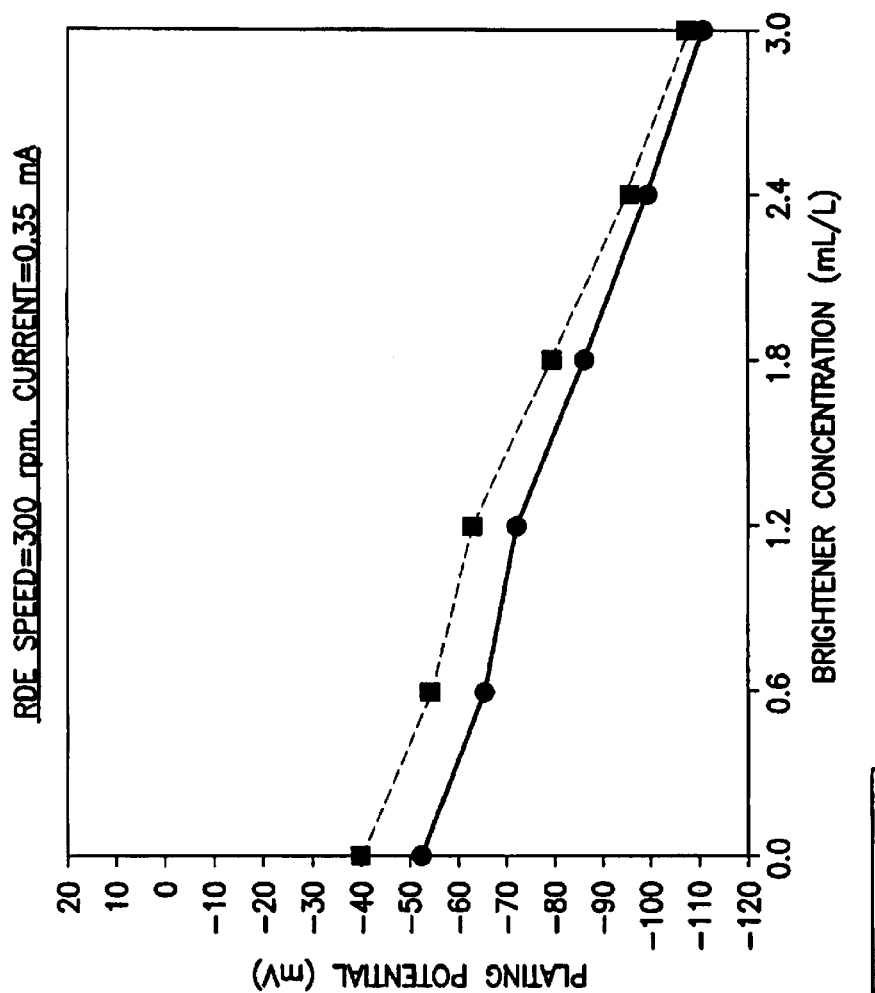
FIGS. 2–4 are graphics that show the impact of electroplating duration on the brightening (i.e., accelerating) effects of the brightener in an aqueous acid copper electroplating solution.

FIG. 2 shows two calibration curves that indicate the brightening effects of a brightener (i.e., accelerator) at various concentrations (from 0 to 3 mL/L) on the plating potential of an aqueous acid copper electroplating solution. One calibration curve is constructed when the rotation speed of the rotating disc electrode (RDE) is set at 300 rpm, and the electroplating duration (i.e., plating time) lasts about 1.2 seconds. The other calibration curve is constructed when the rotation speed is the same (i.e., 300 rpm), but the electroplating duration lasts 15 seconds.

Figure 3:
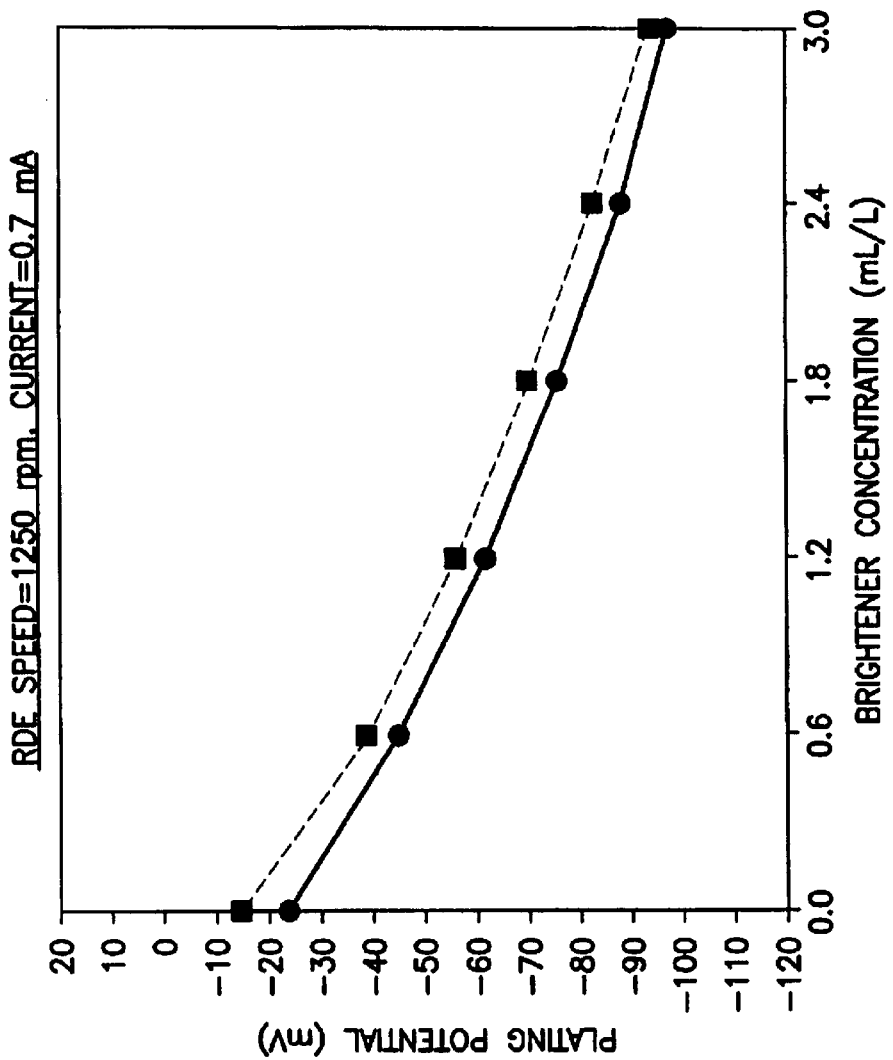

FIG. 3 shows two calibration curves that indicate the brightening effects of the brightener upon the plating potential of the aqueous acid copper electroplating solution, one constructed when the rotation speed is set at 1250 rpm, and the electroplating duration is about 1.2 seconds, and the other constructed when the rotation speed is the same (i.e., 1250 rpm), but the electroplating duration is 15 seconds.

Figure 4:
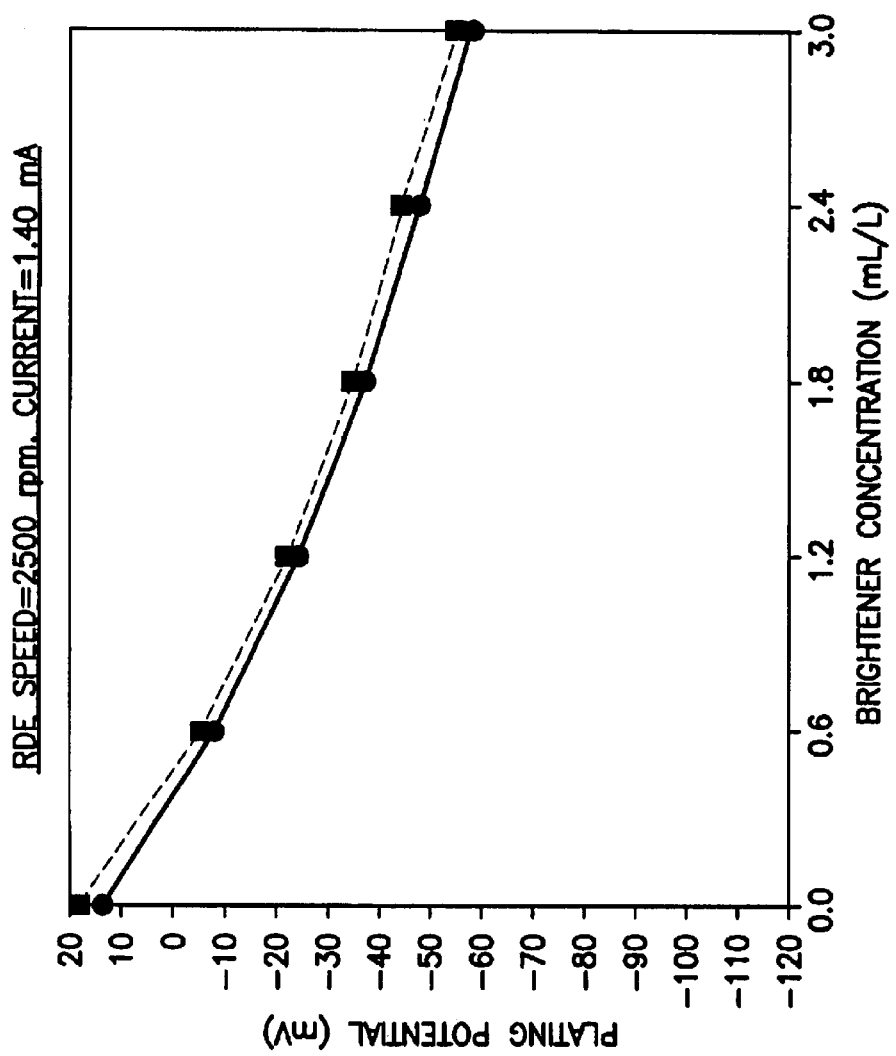

FIG. 4 shows two calibration curves that indicate the brightening effects of the brightener upon the plating potential of the aqueous acid copper electroplating solution, one constructed when the rotation speed is set at 2500 rpm, and the electroplating duration is about 1.2 seconds, and the other constructed when the rotation speed is the same (i.e., 2500 rpm), but the electroplating duration is 15 seconds.

Figure 5:
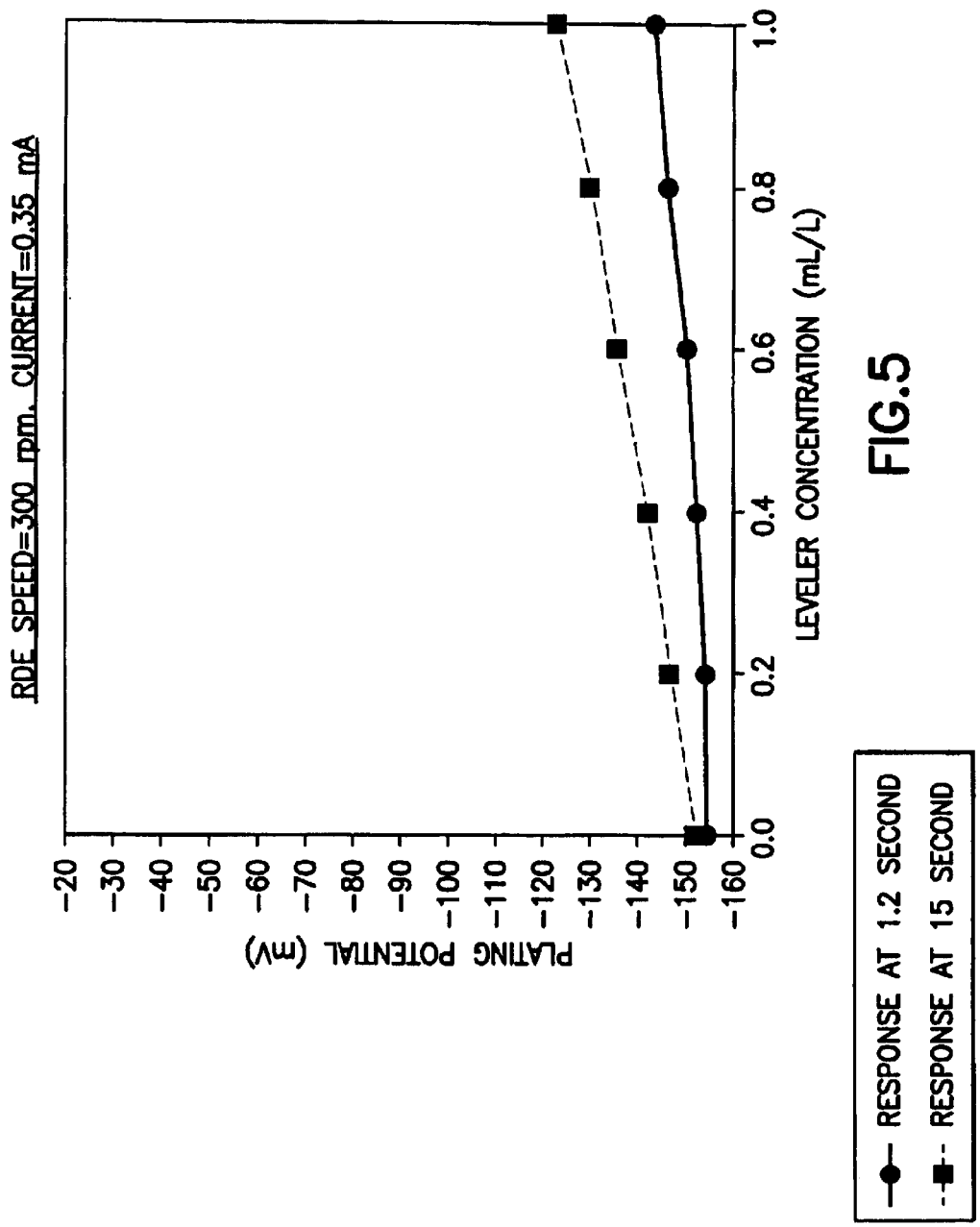
FIGS. 5–7 are graphics that show the impact of electroplating duration on the leveling (i.e., suppressing) effects of the leveler in an aqueous acid copper electroplating solution.

FIG. 5 shows two calibration curves that indicate the leveling effects of a leveler (i.e., suppressor) at various concentrations (from 0 to 1 mL/L) upon the plating potential of an aqueous acid copper electroplating solution. One calibration curve is constructed when the rotation speed of the RDE is set at 300 rpm, and the electroplating duration lasts about 1.2 seconds, and the other calibration curve is constructed when the rotation speed is the same (i.e., 300 rpm), but the electroplating duration is 15 seconds.

Figure 6:
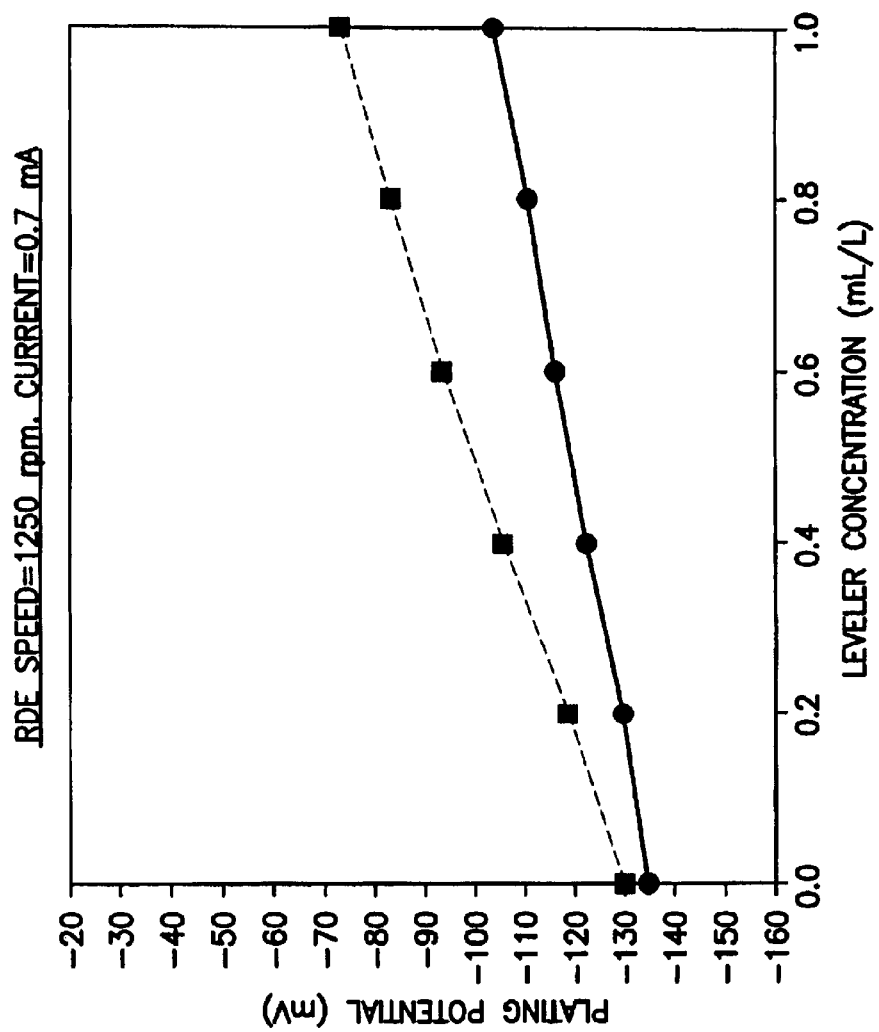

FIG. 6 shows two calibration curves that indicate the leveling effects of the leveler upon the plating potential of the aqueous acid copper electroplating solution, one constructed when the rotation speed is set at 1250 rpm, and the electroplating duration is about 1.2 seconds, and the other constructed when the rotation speed is the same (i.e., 1250 rpm), but the electroplating duration is 15 seconds.

Figure 7:
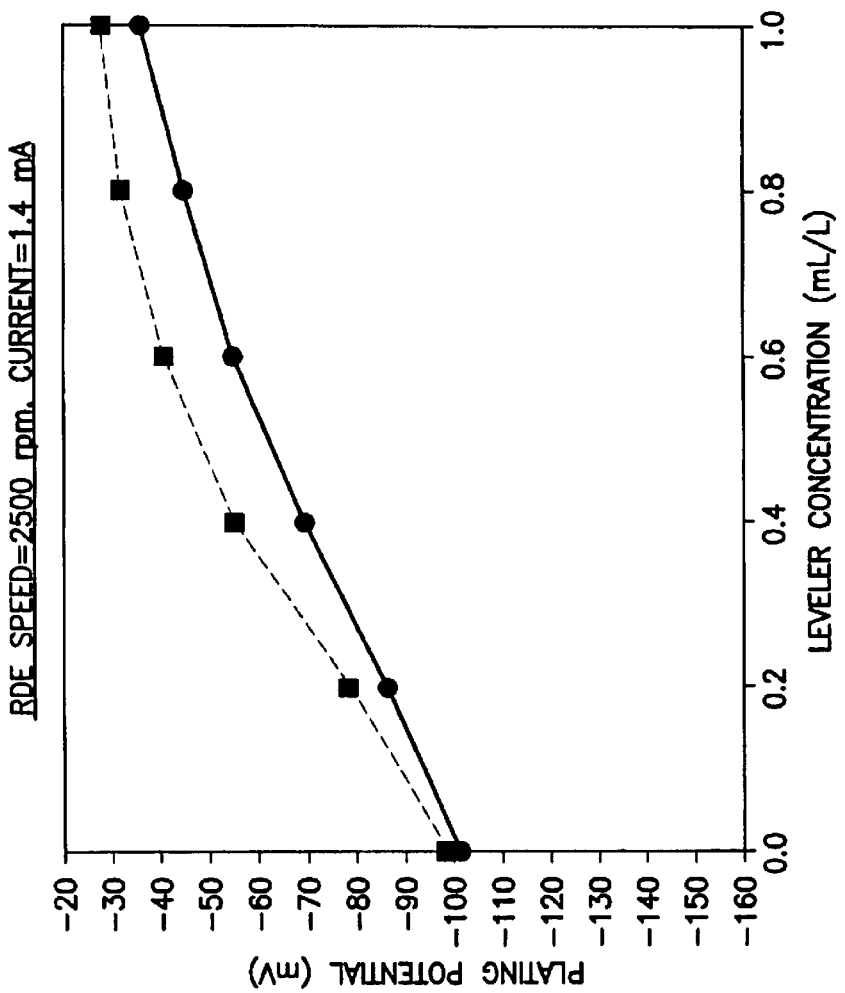

FIG. 7 shows two calibration curves that indicate the leveling effects of the leveler upon the plating potential of the aqueous acid copper electroplating solution, one constructed when the rotation speed is set at 2500 rpm, and the electroplating duration is about 1.2 seconds, and the other constructed when the rotation speed is the same (i.e., 2500 rpm), but the electroplating duration is 15 seconds.

Figure 8:
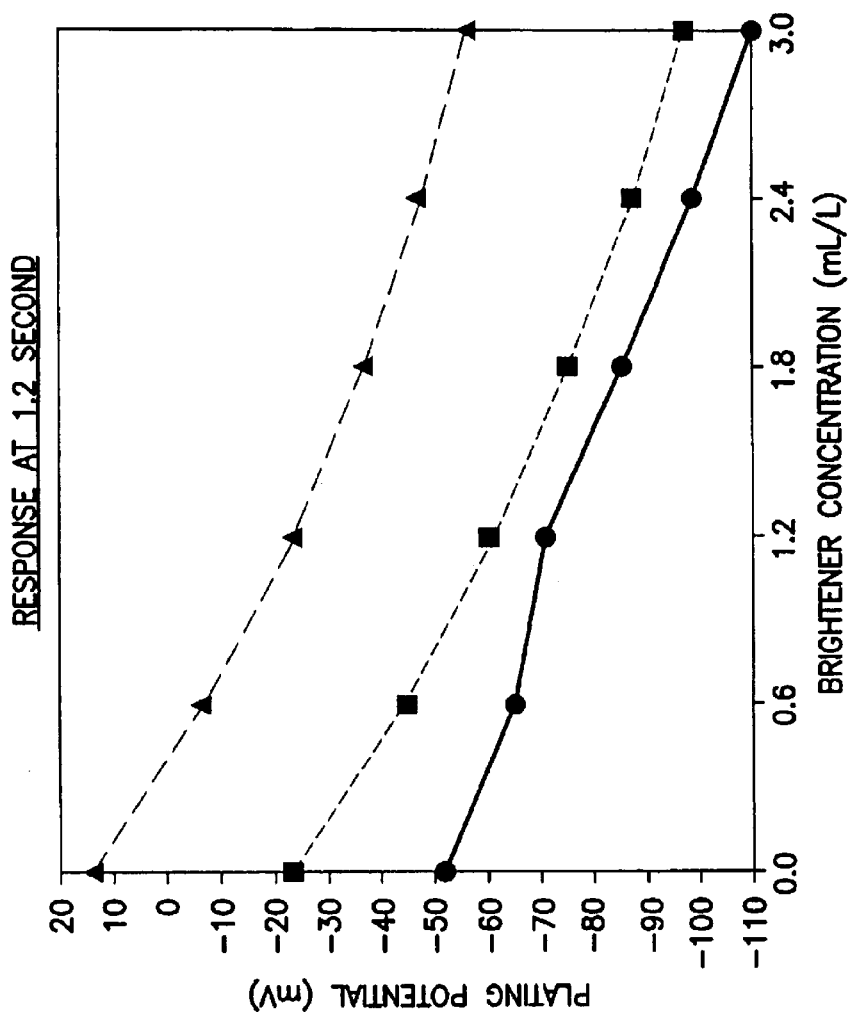
FIGS. 8–9 are graphics that show the impact of rotation speed of the rotating disc electrode (RDE) on the brightening effects of the brightener in an aqueous acid copper electroplating solution.

FIG. 8 shows three calibration curves that indicate the brightening effects of the brightener upon the plating potential of the aqueous acid copper electroplating solution. The first calibration curve is constructed when the rotation speed of the RDE is set at 300 rpm; the second calibration curve is constructed when the rotation speed is set at 1250 rpm; and the third calibration curve is constructed when the rotation speed is set at 2500 rpm. For all three calibration curves, the electroplating duration is set constant for 1.2 seconds.

Figure 9:
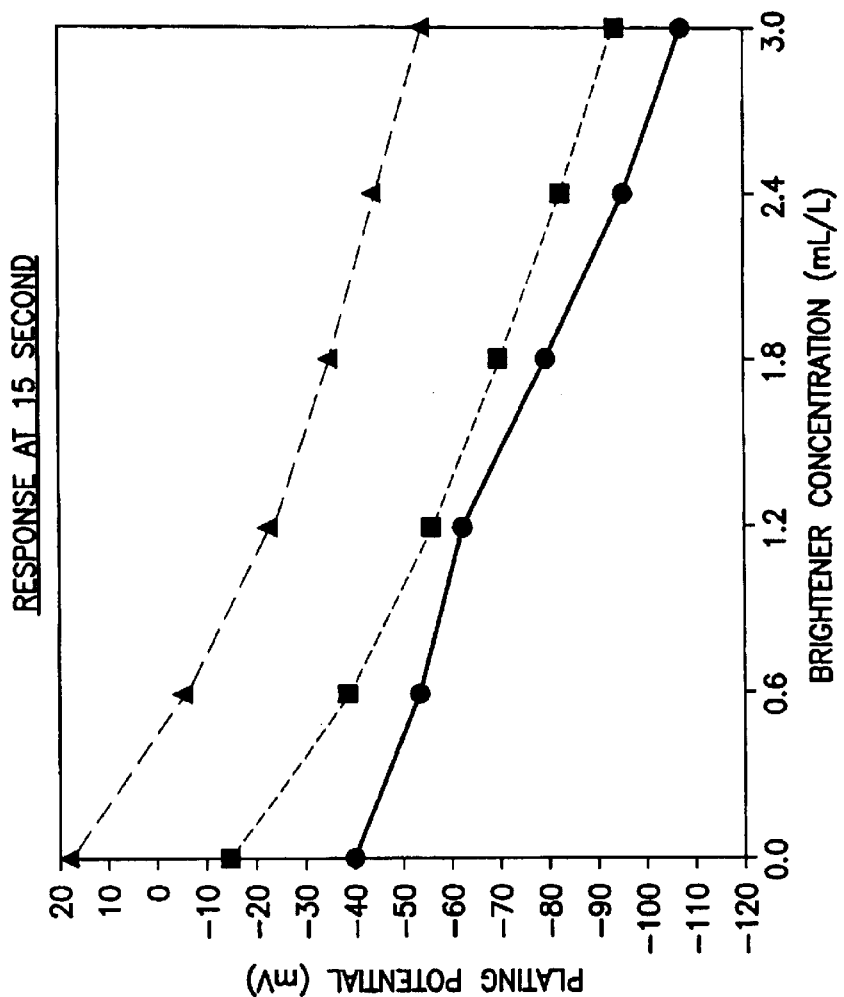

FIG. 9 shows three calibration curves that indicate the brightening effects of the brightener upon the plating potential of the aqueous acid copper electroplating solution, the first calibration curve constructed when the rotation speed of the RDE is set at 300 rpm, the second calibration curve constructed when the rotation speed is set at 1250 rpm, and the third calibration curve constructed when the rotation speed is set at 2500 rpm, while for all three calibration curves, the electroplating duration is set constant for 15 seconds.

Figure 10:
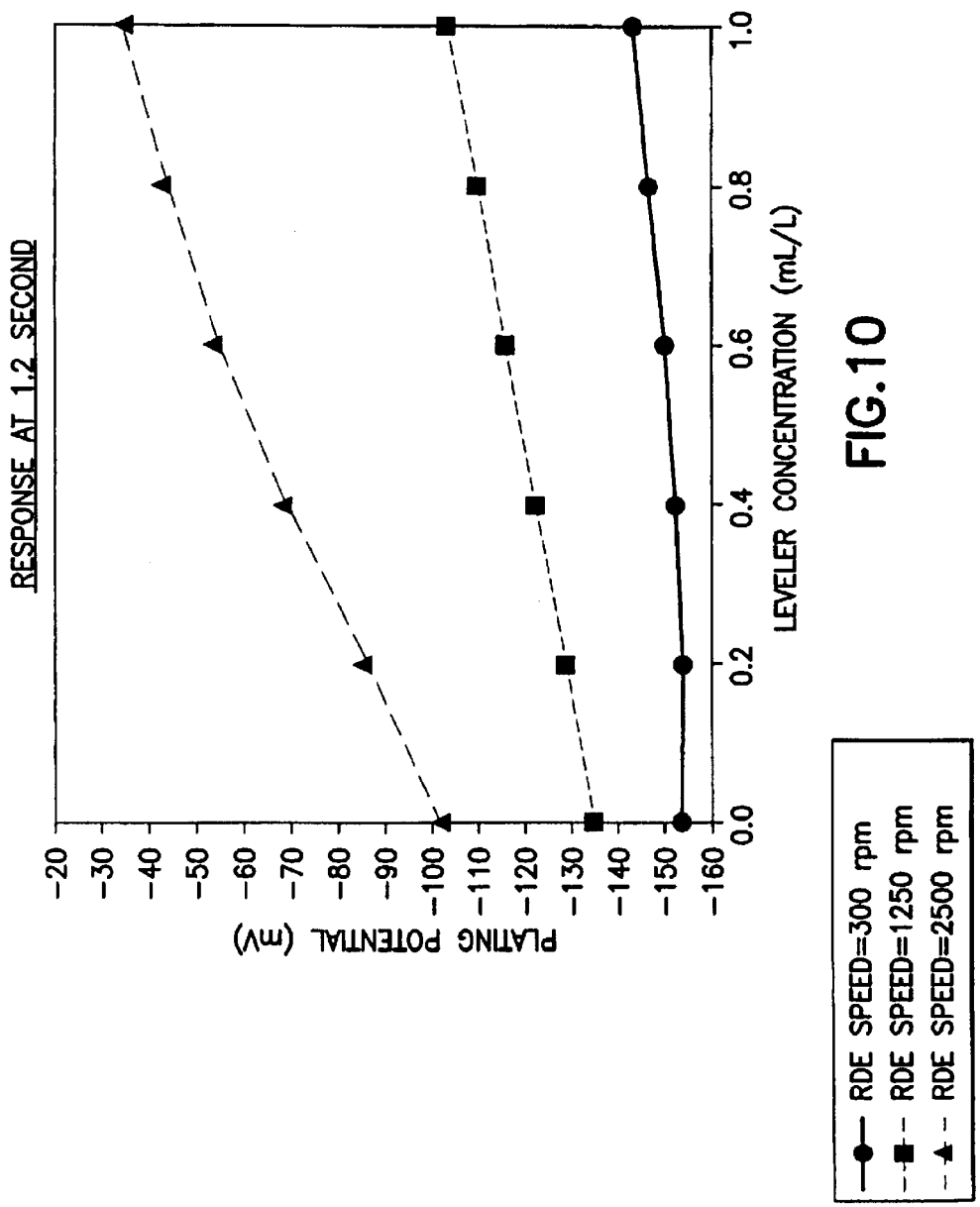
FIGS. 10–11 are graphics that show the impact of rotating speed of the rotating disc electrode (RDE) on the leveling effects of the leveler in an aqueous acid copper electroplating solution.

FIG. 10 shows three calibration curves that indicate the leveling effects of the leveler upon the plating potential of the aqueous acid copper electroplating solution. The first calibration curve is constructed when the rotation speed of the RDE is set at 300 rpm; the second calibration curve is constructed when the rotation speed is set at 1250 rpm; and the third calibration curve is constructed when the rotation speed is set at 2500 rpm. For all three calibration curves, the electroplating duration is set constant for 1.2 seconds.

Figure 11:
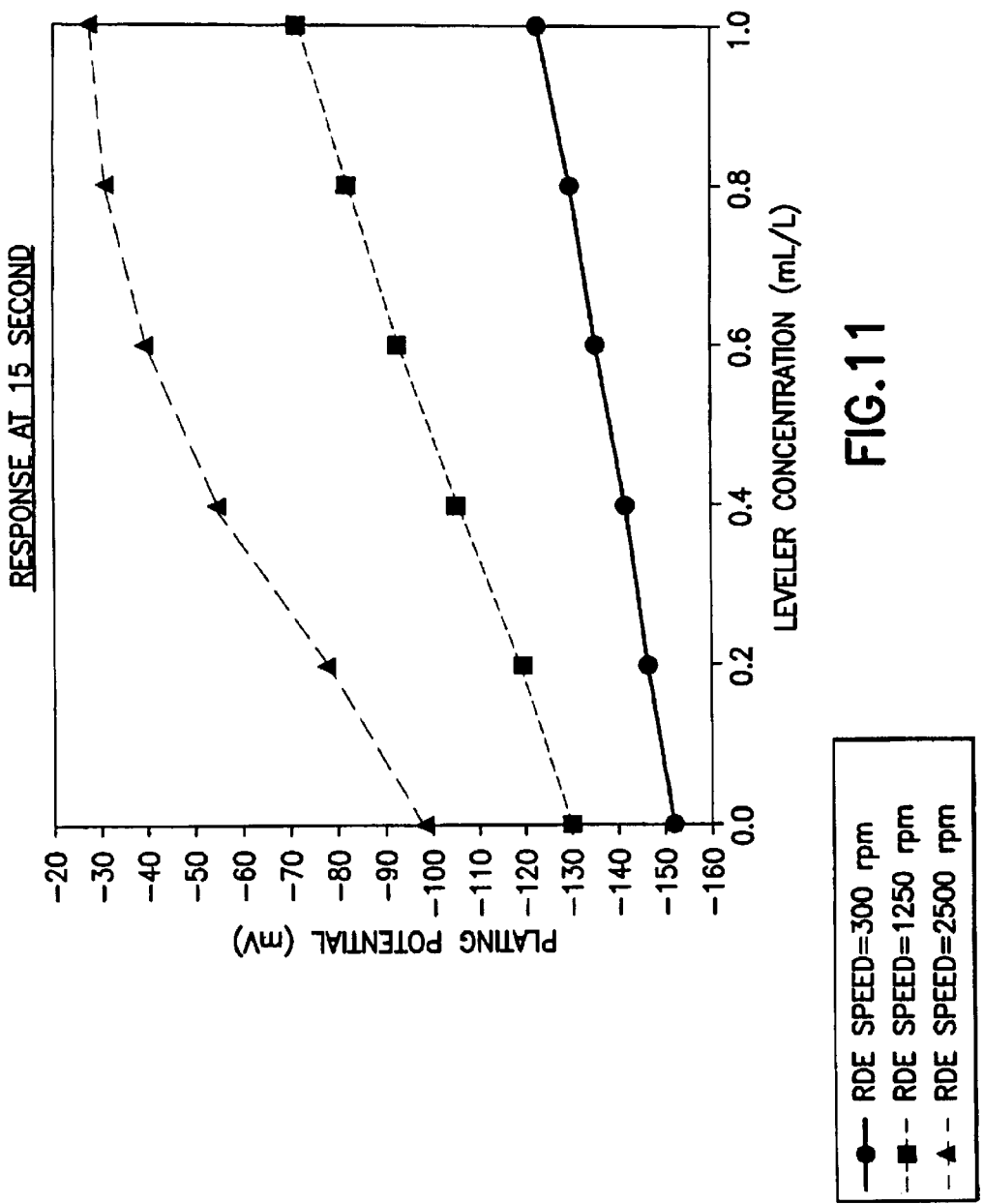

FIG. 11 shows three calibration curves that indicate the leveling effects of the leveler upon the plating potential of the aqueous acid copper electroplating solution, the first calibration curve constructed when the rotation speed of the RDE is set at 300 rpm, the second calibration curve constructed when the rotation speed is set at 1250 rpm, and the third calibration curve constructed when the rotation speed is set at 2500 rpm, while for all three calibration curves, the electroplating duration is set constant for 15 seconds.

FIGS. 2–4 show that by increasing the electroplating duration from 1.2 seconds to 15 seconds, while keeping the RDE speed constant, the brightening (i.e., accelerating) effect of the brightener, as indicated by the slopes of the calibration curves, does not change dramatically. This suggests that the brightening effect of the brightener is independent of the electroplating duration.

FIGS. 5–7, by contrast, show that by increasing the electroplating duration from 1.2 seconds to 15 seconds, while keeping the RDE speed constant, the leveling (i.e., suppressing) effect of the leveler, as indicated by the slopes of the calibration curves, is significantly increased. This suggests that the leveling effect of the leveler is better manifested when the electroplating duration is longer.

Therefore, the present invention in one aspect provides a method for reducing or minimizing the interference between the brightening and the leveling effect, by constructing the calibration curve and measuring the plating potential for the brightener at a shorter electroplating duration, while constructing the calibration curve and measuring the plating potential for the leveler at a longer electroplating duration.

FIGS. 8–9 show that by increasing the rotation speed of the RDE from 300 rpm to 1250 rpm and then to 2500 rpm, while keeping the electroplating duration constant, the brightening effect of the brightener, as indicated by the slopes of the calibration curves, does not change dramatically. This suggests that the brightening effect of the brightener is also independent of the rotation speed of the RDE.

FIGS. 10–11, on the other hand, show that by increasing the rotation speed of the RDE from 300 rpm to 1250 rpm and then to 2500 rpm, while keeping the electroplating duration constant, the leveling effect of the leveler, as indicated by the slopes of the calibration curves, is significantly increased. This suggests that the leveling effect of the leveler is better manifested when the rotation speed of the RDE is set higher.

Therefore, the present invention in another aspect provides a method for reducing or minimizing the interference between the brightening and the leveling effect, by constructing the calibration curve and measuring the plating potential for the brightener at a lower RDE rotation speed, while constructing the calibration curve and measuring the plating potential for the leveler at a higher RDE rotation speed.

The present invention also contemplates a method for minimizing such interference between the brightener and the leveler, by conducting concentration determination for the brightener under a set of measurement conditions that include both lower RDE rotation speed and shorter electroplating duration, and then conducting concentration determination for the leveler under a different set of measurement conditions that include both higher RDE rotation speed and longer electroplating duration.

The concentration of the brightener can be first determined when the rotation speed of the rotating disc test electrode is set within a range of from about 0 rpm to about 4000 rpm, more preferably from about 0 rpm to about 2400 rpm, and the electroplating duration of the plating cycle is set within a range of from about 1 second to about 20 seconds, more preferably from about 1 second to about 10 seconds. The concentration of the leveler can then be determined when the rotation speed of the rotating disc test electrode is preferably set within a range of from about 300 rpm to about 1250 rpm, more preferably from about 500 rpm to about 1250 rpm, and/or the electroplating duration is preferably set within a range of from about 1 second to about 25 seconds, more preferably from about 1 second to about 15 seconds.

Although the invention has been variously disclosed herein with reference to illustrative embodiments and features, it will be appreciated that the embodiments and features described hereinabove are not intended to limit the scope of the invention, and that other variations, modifications and other embodiments will suggest themselves to those of ordinary skill in the art. The invention therefore is to be broadly construed, consistent with the claims hereafter set forth.

What is claimed is:

1. A method for determining concentration of brightener and leveler contained in an aqueous acid metal electroplating solution, comprising the steps of:
   (a) providing a measuring apparatus that comprises:
      (i) a reference electrode;
      (ii) a rotating disc test electrode having a plating surface for depositing metal thereon and a rotational driver for rotating said rotating disc test electrode at a predetermined rotation speed, wherein said rotating disc electrode is disposed in a measurement chamber that comprises an electroplating current source electrode, and wherein the aqueous acid metal electroplating solution is introduced into the measurement chamber for measurement;
      (iii) electroplating-driving electronics that are electrically and operatively coupled between the rotating disc test electrode and the electroplating current source electrode, whereby metal is selectively deposited onto the plating surface of said rotating disc test electrode from the aqueous acid metal electroplating solution in the measurement chamber at a constant known current density; and
      (iv) measuring circuitry electrically and operatively coupled between the rotating disc test electrode and the reference electrode for measuring the electrical potential between the rotating disc test electrode and the reference electrode;
   (b) determining the concentration of brightener in the aqueous acid metal electroplating solution, by using said measuring apparatus to measure a first electrical potential of said metal electroplating solution at a first rotation speed and for a first electroplating duration, and by performing Pulsed Cyclic Galvanostatic Analysis of the first electrical potential measured; and
   (c) determining the concentration of leveler in the aqueous acid metal electroplating solution, by using said measuring apparatus to measure a second electrical potential of said metal electroplating solution at a second rotation speed and for a second electroplating duration, and by performing Pulsed Cyclic Galvanostatic Analysis of the second electrical potential measured, wherein the first rotation speed is lower than the second rotation speed, and wherein the first electroplating duration is shorter than the second electroplating duration.

2. The method of claim 1, wherein the first rotation speed of the rotating disc test electrode is within a range of from about 0 rpm to about 4000 rpm.

3. The method of claim 1, wherein the first rotation speed of the rotating disc test electrode is within a range from about 0 rpm to about 2400 rpm.

4. The method of claim 1, wherein the second rotation speed of the rotating disc test electrode is within a range of from about 300 rpm to about 1250 rpm.

5. The method of claim 1, wherein the second rotation speed of the rotating disc test electrode is within a range of from about 500 rpm to about 1250 rpm.

6. The method of claim 1, wherein the first electroplating duration is within a range of from about 1 second to about 20 seconds.

7. The method of claim 1, wherein the first electroplating duration is within a range of from about 1 second to about 10 seconds.

8. The method of claim 1, wherein the second electroplating duration is within a range of from about 1 second to about 25 seconds.

9. The method of claim 1, wherein the second electroplating duration is within a range of from about 1 second to about 15 seconds.

10. A method for determining concentration of brightener and leveler contained in an aqueous acid metal electroplating solution, comprising the steps of:
    (a) determining concentration of the brightener under a first set of measurement conditions;
    (b) determining concentration of the leveler under a second set of measurement conditions,
    wherein said first set and second set of measurement conditions differ in:
       (i) rotation speed of a rotating disc electrode used for measuring plating potential of said aqueous acid metal electroplating solution; and
       (ii) optionally, electroplating duration at which the plating potential of said aqueous acid metal electroplating solution is measured.

11. The method of claim 10, wherein the first set of measurement conditions includes a rotation speed that is lower than that of the second set of measurement conditions.

12. The method of claim 10, wherein the first set of measurement conditions includes an electroplating duration that is shorter than that of the second set of measurement conditions.

13. The method of claim 10, wherein the first set of measurement conditions includes a first rotation speed and a first electroplating duration, wherein the second set of measurement conditions includes a second rotation speed and a second electroplating duration, wherein the first rotation speed is lower than the second rotation speed, and wherein the first electroplating duration is shorter than the second electroplating duration.

14. The method of claim 13, wherein the first rotation speed is within a range of from about 0 rpm to about 4000 rpm, and wherein the second rotation speed is within a range of from about 300 rpm to about 1250 rpm.

15. The method of claim 13, wherein the first electroplating duration is within a range of from about 1 seconds to about 20 seconds, and wherein the second electroplating duration is within a range of from about 1 seconds to about 25 seconds.

16. A method for determining concentration of a first and a second additives contained in a metal electroplating solution, comprising the steps of:
   (a) determining concentration of the first additive in said metal electroplating solution under a first set of measurement conditions;
   (b) determining concentration of the second additive in said metal electroplating solution under a second set of measurement conditions,
   wherein said first set and second set of measurement conditions differ in:
      (i) rotation speed of a rotating disc electrode used for measuring plating potential of said metal electroplating solution; and
      (ii) optionally, electroplating duration at which the plating potential of said metal electroplating solution is measured.

17. The method of claim 16, wherein the first additive is a brightener, and the second additive is a leveler.

18. The method of claim 17, wherein the first set of measurement conditions has a rotation speed that is lower than that of the second set of measurement conditions, and an electroplating duration that is shorter than that of the second set of measurement conditions.

19. The method of claim 18, wherein the first set of measurement conditions has a rotation speed that is within a range of from about 0 rpm to about 4000 rpm, and the second set of measurement conditions has a rotation speed that is within a range of from about 300 rpm to about 1250 rpm.

20. The method of claim 18, wherein the first set of measurement conditions has an electroplating duration that is within a range of from about 1 second to about 20 seconds, and the second set of measurement conditions has an electroplating duration that is within a range of from about 1 seconds to about 25 seconds.

* * * * *